United States Patent [19]
Olsson et al.

[11] Patent Number: 5,769,072
[45] Date of Patent: Jun. 23, 1998

[54] ANESTHETIC SYSTEM WITH MULTIPLE VALVE-CONTROLLED BELLOWS

[75] Inventors: Sven-Gunnar Olsson, Arlov; Göran Rydgren, Bunkeflostrand; Kalman Csiki, Landskrona, all of Sweden

[73] Assignee: Siemens Elema AB, Solna, Sweden

[21] Appl. No.: 819,834

[22] Filed: Mar. 18, 1997

[30] Foreign Application Priority Data

Mar. 20, 1995 [SE] Sweden .................................. 9601065

[51] Int. Cl.⁶ ............................ A62B 7/04; A61M 16/00; F16K 31/02
[52] U.S. Cl. ................................ 128/205.13; 128/204.28; 128/205.15; 128/205.16; 128/205.17; 128/204.22
[58] Field of Search ........... 128/204.28, 205.13–205.17, 128/204.22, 205.24, 205.26, 205.28

[56] References Cited

U.S. PATENT DOCUMENTS

| | | | |
|---|---|---|---|
| 2,216,183 | 10/1940 | Connell | 128/205.16 |
| 2,711,170 | 6/1955 | Bornstein | 128/205.13 |
| 3,499,438 | 3/1970 | Manley | 128/205.15 |
| 3,523,527 | 8/1970 | Foster | 128/205.16 |
| 3,789,837 | 2/1974 | Phillips et al. | 128/205.16 |
| 3,890,967 | 6/1975 | Elam et al. | 128/205.17 |
| 3,921,628 | 11/1975 | Smythe et al. | 128/205.13 |
| 3,923,053 | 12/1975 | Jansson | 128/205.13 |
| 4,299,216 | 11/1981 | Bernard et al. | 128/205.17 |
| 4,905,685 | 3/1990 | Olsson et al. . | |

FOREIGN PATENT DOCUMENTS 462 366  6/1990  Sweden .

*Primary Examiner*—Kimberly L. Asher
*Attorney, Agent, or Firm*—Hill & Simpson

[57] ABSTRACT

An anesthetic system has an external gas reservoir and three gas bellows arranged in the external gas reservoir to alternatingly collect or deliver breathing gas from and to a ventilator unit. In this manner a completely closed system is achieved with minimal consumption of, primarily, anesthetic. The bellows are regulated by a regulatory unit which, via a valve system, can selectively connect a source of drive gas to one or more of the containers in order to compress the gas bellows respectively contained therein. When no drive gas is supplied, each bellows passively expands.

10 Claims, 2 Drawing Sheets

ANESTHETIC SYSTEM WITH MULTIPLE VALVE-CONTROLLED BELLOWS

BACKGROUND OF THE INVENTION

1. Field of the Invention

The present invention relates to an anesthetic system of the type wherein expired respiratory gas is recirculated, after $CO_2$ removal for re-use in an inspiratory phase by the subject.

2. Description of the Prior Art

U.S. Pat. No. 4,905,685 describes an anesthetic system in which a ventilator unit supplies a patient with breathing gas through an inspiratory line and evacuates expired breathing gas through an expiratory line. Expired breathing gas is passed through a number of filters which remove carbon dioxide and water vapor from the breathing gas. The expired breathing gas is then sent to a compressor which compresses the expired breathing gas at a predetermined positive pressure, and compressed breathing gas is sent to a gas reservoir. This gas reservoir is, in turn, connected to the ventilator unit and supplies the ventilator unit with breathing gas. With respect to the patient, the anesthetic system operates as an open breathing system in which the ventilator unit regulates the composition of the breathing gas as well as the pressure and/or flow of breathing gas to the patient. The ventilator unit is also able to regulate expiration and e.g. establish a positive end expiratory pressure (PEEP). The anesthetic system as a whole, however, is completely closed. All expired breathing gas is ultimately re-used after being filtered, compressed and returned to the gas reservoir. Compensation for gases taken up by the patient, oxygen in particular, can be made separately with gas supplied to the ventilator unit from an external source.

The use of a compressor, however, adds an additional power-consuming unit to the anesthetic system, and the noise level produced by the compressor will be relatively high. A number of different 35 valves for regulating the compressed breathing gas must also be provided in the system.

SUMMARY OF THE INVENTION

An object of the present invention is to provide an anesthetic system which avoids the aforementioned problems.

The above object is achieved in accordance with the principles of the present invention in an anesthetic system of the type described above wherein expired breathing gas, after removal of gaseous pollutants such as carbon dioxide and/or water vapor is circulated for re-use by a patient, and having at least two volume variable gas receptacles connected to the ventilator outlet via a first valve system and to the ventilator inlet via a second valve system, for controlling the direction of breathing gas flow, and also including a regulatory unit arranged in the volume variable gas receptacles for alternatingly emptying one of those receptacles at a time in order to supply expired breathing gas to the ventilator inlet, at the same time as one of the other receptacles collects expired breathing gas from the outlet.

When at least two volume variable gas receptacles, which are alternatingly filled with and emptied of expired breathing gas, are used, there is no need for a compressor. The pressure of expired breathing gas is sufficient for passive filling of a volume-variable gas receptacle. Another volume-variable gas receptacle is compressed at the same time, so previously expired breathing gas is compressed and sent to the ventilator unit for re-use.

In one embodiment of the anesthetic system, the volume-variable gas receptacles are each a gas-tight bellows arranged in a gas-tight container. The gas-tight containers can be pressurized by a drive gas. When a bellows is to be emptied of expired breathing gas, drive gas is fed into the container, and the bellows is compressed by the positive pressure. The pressure of the supplied breathing can be regulated by regulating the pressure of the drive gas. Other bellows, arranged in containers to which no drive gas is supplied, can expand and f ill with expired breathing gas. The bellows can be equipped with a weight which contributes to uniform bellows expansion and also helps counteract resistance to flow in the line system.

As an alternative to weights, each container can be connected to a vacuum pump which evacuates air from the container and generates a negative pressure, in relation to the pressure of the breathing gas, in the container.

The bellows will then actively expand as a result of the generated pressure gradient.

In another embodiment of the anesthetic system, a mechanical drive mechanism is arranged by the volume-variable gas receptacles to compress and expand them.

DESCRIPTION OF THE PREFERRED EMBODIMENTS

Figure 1:
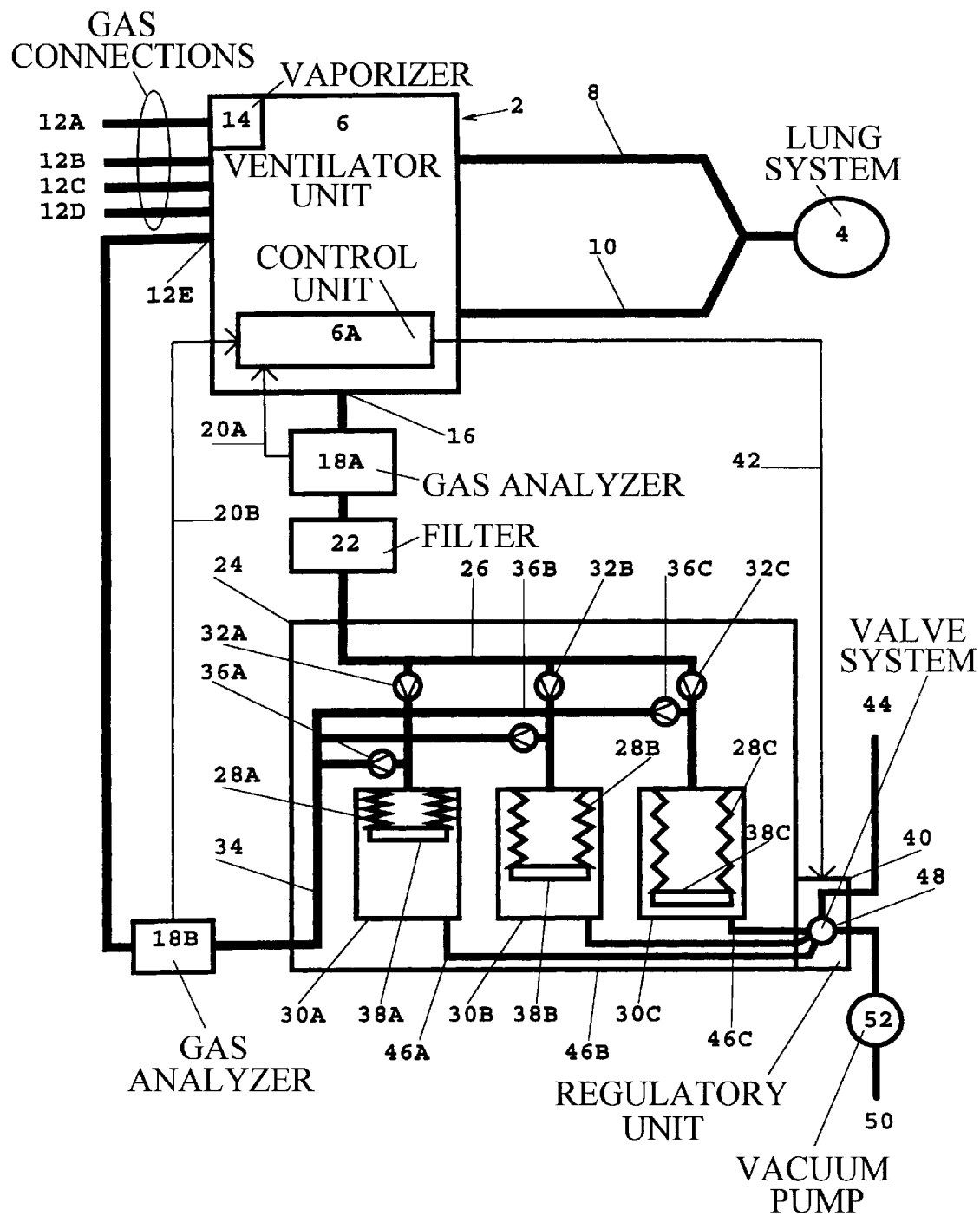
FIG. 1 shows a first embodiment of an anesthetic system constructed in accordance with the principles of the present invention.

One embodiment of the anesthetic system according to the invention is designated 2 in FIG. 1. The anesthetic system 2 is connected to a patient 4 to supply breathing gas to and remove breathing from the patient 4. The anesthetic system 2 includes a ventilator unit 6 which supplies a flow of gas to the patient 4 through an inspiratory line 8 and removes breathing gas from the patient 4 through an expiratory line 10. The ventilator system 6 can operate in different modes, depending on whether the patient 4 is breathing spontaneously, only needs breathing support, or requires controlled ventilation. In principle, this depends on which phase of anesthesia the patient 4 is in.

Breathing gas supplied to the patient 4 is prepared in the ventilator unit 6. A first gas connection 12A, a second gas connection 12B, a third gas connection 12C, a fourth gas connection 12D and a fifth gas connection 12E are connected to the ventilator unit 6 to supply the gas components to be mixed in forming the breathing gas.

A small flow of e.g. oxygen ($O_2$) can be carried to a vaporizer 14 in the ventilator unit 6 through the first gas connection 12A. Anesthetic in liquid form is stored in the vaporizer 14. When a specific flow of oxygen is passed through the vaporizer 14, a specific amount of anesthetic can be carried along with it. A large f low is required in the initial stage of anesthesia, since a large amount of anesthetic must then be supplied to the patient 4. Thereafter, only the amount of anesthetic needed to compensate for the uptake of anesthetic in the patient 4 is vaporized. Oxygen can also be supplied through the second gas connection 12B, nitrous oxide ($N_2O$) can be delivered through the third gas connection 12C, ordinary air can be supplied through the fourth gas connection 12D and previously expired and filtered breathing gas can be returned to the ventilator unit 6 through the fifth gas connection 12E.

This array of gas connections 12A–12E makes possible rapid changes in the composition of the breathing gas.

In respect to the patient 4, the ventilator unit 6 functions as an open system, i.e. flow paths for inspiration and expiration are completely separated in the ventilator unit 6 and between the ventilator unit 6 and the patient 4. Gas supplied to the ventilator 6, through the gas connections 12A–12E, is mixed in specific proportions to form a predefined composition for the breathing gas and then sent to the patient 4. During expiration, breathing gas is evacuated from the patient 4 via the ventilator unit 6.

As a system, however, the anesthetic system 2 is completely closed. Expired breathing gas is carried from an outlet 16 in the ventilator unit 6 through a first gas analyzer 18A. The concentration of at least one gas component, preferably a plurality of components such as $O_2$, $CO_2$, $N_2O$ and the anesthetic gas, is measured in the first gas analyzer 18A. A measurement value corresponding to the concentration is sent to the control unit 6A of the ventilator unit 6 via a first signal line 20A. Expired breathing gas then passes a filter 22 which removes at least carbon dioxide, and preferably even water vapor, from the breathing gas. The filter can contain e.g. zeolites or some other absorbent substance. Expired breathing gas is then sent to an external gas reservoir 24.

The gas reservoir 24 serves as a breathing gas depot in which breathing gas expired by the patient 4 is collected for subsequent delivery to the ventilator unit 6. A line 26 in the gas reservoir 24 is connected to a first gas-tight bellows 28A, a second gas-tight bellows 28B and a third gas-tight bellows 28C. Expired breathing gas can be sent to one or a number of bellows 28A, 28B and 28C. The bellows 28A, 28B and 28C are devised for passive expansion in order to receive breathing gas from the ventilator unit 6, and breathing gas under pressure is returned to the ventilator unit 6 when the bellows are actively compressed. The pressure of the breathing gas depends on the degree to which the bellows 28A, 28B and 28C are compressed.

In order to achieve active compression of the bellows 28A, 28B and 28C, each gas-tight bellows 28A, 28B and 28C is arranged in a gas-tight container 30A, 30B and 30C. A drive gas can be applied to one or more of the containers 30A, 30B and 30C, at the same time. As FIG. 1 shows, the first bellows 28A in the first container 30A is almost fully compressed, the second bellows 28B in the second container 30B is in the process of filling with breathing gas and the third bellows 28C in the third container 30C is already filled with expired breathing gas.

In order to control the direction of flow of expired breathing gas in the gas reservoir 24, a first check valve 32A, a second check valve 32B and a third check valve 32C are arranged between the gas line 26 and the respective container 28A, 28B and 28C. Thus, gas can only flow from the outlet 16 of the ventilator 6 to one or more of the containers 28A, 28B and 28C. Downstream from the check valves 32A, 32B and 32C, a second gas line 34 is connected to the respective bellows 28A, 28B and 28C to carry breathing gas to the gas connection 12E in the ventilator 6 when a bellows 28A, 28B or 28C is compressed.

The breathing gas passes a second gas analyzer 18B which also measures the concentration of at least one component in the breathing gas and sends the measurement result to the control unit 6A in the ventilator unit 6 via a second signal line 20B. Measurement before breathing gas is returned to the ventilator unit 6 is performed as an additional check on the composition of the new breathing gas to be mixed in the ventilator unit 6 with previously expired breathing gas as the basic component. The second gas analyzer 18B should therefore measure the concentration of all the relevant gas components, such as $O_2$, $N_2O$ and the anesthetic gas. $CO_2$ can also be measured as a safety precaution to check the filter 22.

To keep breathing gas from being sent to any of the other bellows 28B or 28C, gas during compression of e.g. the first bellows 28A, a fourth check valve 36A, a fifth check valve 36B and a sixth check valve 36C are arranged between the second gas line 34 and the respective bellows 28A, 28B and 28C. To facilitate expansion of the bellows 28A, 28B and 28C while simultaneously overcoming resistance to flow in the lines between the patient 4 and the gas reservoir 24, each bellows 28A, 28B and 28C is equipped with a weight 38A, 38B and 38C which forces the bellows 28A, 28B and 28C to expand when no drive gas is applied to the container 30A, 30B and 30C.

Compression of the bellows 28A, 28B and 28C is controlled by a regulatory unit 40. The regulatory unit 40 is controlled, in turn, by the control unit 6A in the ventilator unit 6, and control signals are sent from the control unit 6A via a control line 42. A drive gas connection 44 is connected to the regulatory unit 40 to carry drive gas under high pressure. This drive gas can then be connected, via a valve system 48, to the first container 30A via a first drive gas line 46A, to the second container 30B via a second drive gas line 46B and to the third container 30C via a third drive gas line 46C. A pressure regulator (not shown) can also be arranged in the regulatory unit 40 to regulate the pressure of the drive gas sent to the containers 30A, 30B and 30C. The regulatory unit 40 normally operates so that only one container 30A, 30B or 30C at a time is pressurized, the other two being connected to ambient atmosphere via an outlet line 50.

A vacuum pump 52 can also be connected to the outlet line 50. The vacuum pump 52 can replace the weights 38A, 38B and 38C for achieving uniform expansion of the bellows 28A, 28B and 28C. A negative pressure is then generated in the containers 30A, 30B and 30C when they are filled with breathing gas from the outlet 16. The vacuum pump 52 can also be used for selectively connecting a specific container 30A, 30B 30C for filling it with breathing gas. The latter can be used when the total amount of gas in the anesthetic system 2 does not need to be very large.

Figure 2:
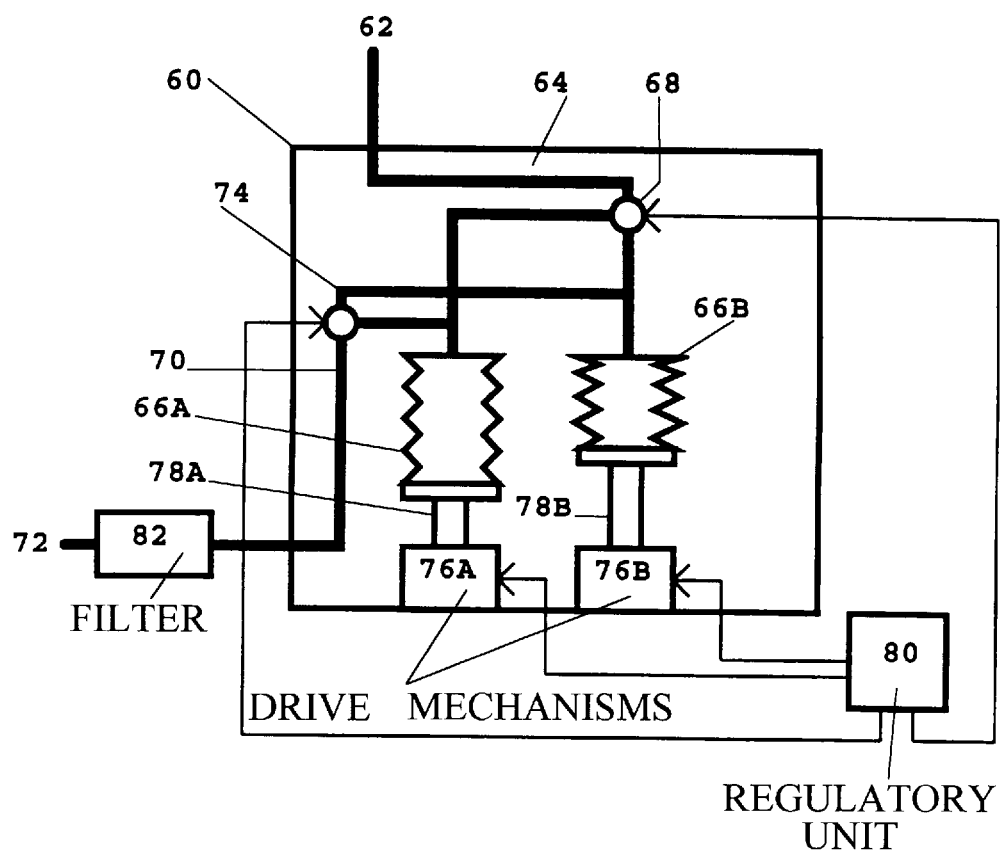
FIG. 2 shows an alternative embodiment of a gas reservoir in the anesthetic system constructed in accordance with the principles of the present invention.

FIG. 2 shows an alternative embodiment of the external gas reservoir, designated 60. Expired breathing gas is carried through a gas inlet 62 to a first gas line 64 in the gas reservoir 60. The first gas line 64 is connected to a first gas bellows 66A and a second gas bellows 66B via a first switching valve 68. The first switching valve 68 is switchable so only one of the gas bellows 66A or 66B at a time can be connected to the first gas line 64. In this embodiment, one gas bellows 66A or 66B at a time is actively filled with breathing gas. A second gas line 70 is also connected to the gas bellows 66A or 66B to carry evacuated breathing gas to a gas outlet 72 and on to a ventilator unit (not shown). A second switching valve 74 is arranged between the second gas line 70 and the gas bellows 66A and 66B. The second switching valve 74 is switchable so only one gas bellows 66A and 66B at a time can be connected to the second gas line 70.

The switching valves 68 and 74 are controlled so the first gas bellows 66A is connected to the first gas line 64 when the second gas bellows 66B is connected to the second gas line 70 15 and vice-versa. The switching valves 68 and 74 are then alternatingly switched so the gas bellows 66A, 66B can be alternatingly filled and emptied.

In this embodiment, the gas bellows 66A and 66B are mechanically controlled by a first drive mechanism 76A which, via a first control rod 78A, regulates the volume of the first gas bellows 66A, and a second drive mechanism 76B which, via a second control rod 78B, regulates the volume of the second gas bellows 66B. The drive mechanisms 76A and 76B are controlled by a regulatory unit 80. When e.g. the first gas bellows 66A is to be filled with expired breathing gas, the first drive mechanism 76A is activated so the first control rod 78A is pulled downwardly. This causes the first gas bellows 66A to expand, and a negative pressure develops inside the first gas bellows 66A. Expired breathing gas is then withdrawn by suction from the first gas line 64 into the first gas bellows 66A.

At the same time, the second drive mechanism 76B is regulated so the second control rod 78B compresses the second gas 35 bellows 66B. Breathing gas in the second gas bellows 66B is then pushed toward the gas outlet 72.

Regulation of the drive mechanisms 76A and 76B can also be performed so they are only activated during expiration and during expansion of the gas bellows 66A, 66B, so as to facilitate the patient's exhalation. Between expirations, the gas bellows 66A and 66B are allowed to expand passively.

FIG. 2 also shows a filter 82, arranged in the second gas line 70, for removal of e.g. $CO_2$ from breathing gas. Placement of the filter 82 after the gas reservoir 60 produces the advantage that the resistance of the filter 82 to the flow of breathing gas is easily overcome by compressing the gas bellows 66A and 66B. At the same time, flow resistance is reduced upstream from the gas reservoir 60, thereby making it easier for the patient to exhale.

The two embodiments of the gas reservoir described above in FIGS. 1 and 2 can be combined in appropriate ways. Thus, the gas reservoir 24 in FIG. 1 can contain two gas bellows 28A and 28B. A combination of 28A, 28B. A combination of compressed air and mechanical regulation of the volume of the bellows is also possible. Check valves can replace the switching valves 68 and 74 in FIG. 2. The filter 22 can be located downstream from the gas reservoir 24 in FIG. 1.

The various bellows can be replaced by some other type of volume-variable gas receptacles, such as pistons or balloons, arranged to be compressed between plates.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anesthetic system comprising:

an inspiratory line adapted for carrying breathing gas containing an anesthetic to a lung system, an expiratory line adapted for carrying expired breathing gas from a lung system;

a ventilator unit having an inlet for receiving at least a portion of said breathing gas and for delivering said at least a portion of said breathing gas to said inspiratory line, and an outlet for removing expired breathing gas carried in said expiratory line;

a gas reservoir comprising at least two volume variable gas receptacles connected to said outlet via a first valve system and connected to said inlet via a second valve system for controlling a direction of flow of said breathing gas;

regulatory means acting on said volume variable gas receptacles for alternatingly emptying one of said volume-variable gas receptacles at a time for supplying expired breathing gas to said inlet and for simultaneously collecting expired breathing gas from said outlet in another of said volume variable gas receptacles; and filter means for removing at least one gaseous pollutant from said expired breathing gas before said expired breathing gas is returned to said inlet.

2. An anesthetic system as claimed in claim 1 wherein said first valve system comprises a plurality of check valves respectively connected between said volume variable gas receptacles and said outlet, and wherein said second valve system comprises a plurality of further check valves connected between said volume variable gas receptacles and said inlet.

3. An anesthetic system as claimed in claim 1 wherein each volume-variable gas receptacle comprises a bellows.

4. An anesthetic system as claimed in claim 3 comprising a plurality of gas-tight containers respectively containing said bellows, and wherein said regulatory means comprises a source of drive gas connected to said containers via a third valve system for alternatingly delivering said drive gas under controllable pressure to one of said containers at a time for compressing the bellows therein while simultaneously releasing drive gas from at least one other of said containers for allowing the bellows in said at least one other of said containers to expand.

5. An anesthetic system as claimed in claim 4 wherein each bellows has a weight attached to a bottom thereof for uniformly expanding the bellows when no drive gas is applied to the container containing that bellows.

6. An anesthetic system as claimed in claim 4 wherein said regulatory means further comprises vacuum pump means, connected to each of said containers via said third valve system, for producing a negative pressure in said containers for actively expanding the bellows in each container.

7. An anesthetic system as claimed in claim 1 wherein said regulatory means comprises a mechanical drive mechanism for controlling compression and expansion of said volume variable gas receptacles.

8. An anesthetic system as claimed in claim 1 further comprising gas analyzer means for measuring a concentration of at least one component in said breathing gas at at least one measurement point in said anesthetic system.

9. An anesthetic system as claimed in claim 1 wherein said filter means is connected between said volume-variable gas receptacles and said inlet.

10. An anesthetic system as claimed in claim 1 wherein said filter means contains zeolite crystals.

* * * * *